United States Patent [19]

Stark

[11] Patent Number: 4,525,346
[45] Date of Patent: Jun. 25, 1985

[54] AQUEOUS ANTIMICROBIAL OPHTHALMIC SOLUTIONS

[75] Inventor: Raymond L. Stark, Midland, Mich.

[73] Assignee: Alcon Laboratories, Inc., Fort Worth, Tex.

[21] Appl. No.: 537,331

[22] Filed: Sep. 29, 1983

Related U.S. Application Data

[63] Continuation-in-part of Ser. No. 509,281, Jun. 29, 1983, abandoned, which is a continuation of Ser. No. 306,317, Sep. 28, 1981, Pat. No. 4,407,791.

[51] Int. Cl.$^3$ ............... A61K 31/74; A61K 31/79; A61K 31/14
[52] U.S. Cl. ............................. 424/80; 424/78; 514/642
[58] Field of Search ............... 424/78, 329, 80; 564/295

[56] References Cited

U.S. PATENT DOCUMENTS

| | | | |
|---|---|---|---|
| 3,639,576 | 2/1972 | Kaspar et al. | 424/78 |
| 3,882,036 | 5/1975 | Krezanoski et al. | 424/78 |
| 3,961,042 | 6/1976 | Green et al. | 424/78 |
| 3,966,904 | 6/1976 | Green et al. | 424/78 |
| 4,005,193 | 1/1977 | Green et al. | 424/78 |
| 4,012,446 | 3/1977 | Green et al. | 564/295 |
| 4,026,945 | 5/1977 | Green et al. | 424/329 |
| 4,027,020 | 5/1977 | Green et al. | 424/329 |
| 4,029,817 | 6/1977 | Blanco et al. | 424/329 |
| 4,036,959 | 7/1977 | Green et al. | 424/329 |
| 4,091,113 | 5/1978 | Green et al. | 424/329 |

OTHER PUBLICATIONS

Onamer-M-A Product Bulletin LRSBD 12177, Onyx Chemical Company, New York, N.Y.
Refojo, 1972, "Reversible Binding of Chlorhexidine Gluconate to Hydrojel Contact Lenses"; *Contact and Intraocular Lens Med. J.*, 2, pp. 47–56.
Petrocci et al., 1978 "Quaternary Ammonium Antimicrobial Compounds:Old and New", Developments in Industrial Microbiology 20:11–14.
Richardson et al., 1978, "The Interaction of Preservatives with Polyhydroxyethylmethacrylate(-PolyHEMA)", *J. of Pharm. Pharmac.*, 30:469–475.
Kaspar, 1976, "Binding Characteristics and Microbiological Effectiveness of Preservatives", *Australian Journal of Optometry*, pp. 3–8.
Letter from Petrocci to Randeri dated Oct. 19, 1981.

*Primary Examiner*—Douglas W. Robinson
*Attorney, Agent, or Firm*—Fitch, Even, Tabin & Flannery

[57] ABSTRACT

This invention relates to ophthalmic compositions which comprise quaternary ammonium salt having the formula

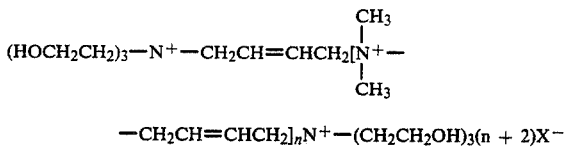

$$-CH_2CH=CHCH_2]_nN^+-(CH_2CH_2OH)_3(n + 2)X^-$$

wherein X = a pharmaceutically acceptable anion, such compositions providing aqueous disinfecting solutions for contact lenses as well as a preserved ocular compositions including contact lens treating solutions comfort drop solutions, preserved saline solutions, ointments and other ocular medicaments.

25 Claims, No Drawings

AQUEOUS ANTIMICROBIAL OPHTHALMIC SOLUTIONS

This is a continuation-in-part application of application Ser. No. 509,281 filed June 29, 1983, now abandoned, the latter application being a continuation of application No. 306,317 filed Sept. 28, 1981 now U.S. Pat. No. 4,407,791.

This invention relates to ophthalmic disinfecting and preserving compositions. More particularly, this invention relates to preserving ophthalmic solutions, ointments and suspensions and to solutions for treating and disinfecting both soft and hard contact lenses.

Soft contact lenses have been a comparatively recent development. Soft contact lenses can be divided into two broad categories, namely, hydrophilic and hydrophobic contact lenses. The care of each of these lenses presents special problems.

Hydrophilic soft contact lenses are hydrated gel lenses which are prepared by copolmerizing hydrophilic organic monomers having an olefinic double bond with a small amount of cross-linking agent, usually having two polymerizable, olefinic double bonds. These lenses are usually based upon poly(hydroxyalkyl)methacrylates such as poly(hydroxyethyl)methacrylate, cross-linked with, for example, ethylene glycol dimethacrylate a hydroxyethyl dimethacrylate. The hydroxyl groups of the hydrated gel lenses render the lenses hydrophilic, i.e. they wet easily and absorb water. With this water absorption, the lenses also may take up chemicals dissolved in the water.

The hydrated gel lens, due to its gel structure and/or its affinity to adsorb or absorb materials, may complex and concentrate most known preservatives used to disinfect and preserve the lens. The most common preservatives are thimerosal, benzalkonium chloride and chlorhexidine. These compounds are toxic to the eye and may cause corneal erosion and corneal ulceration resulting in pain and exposed nerve endings. It has been found that these preservatives become concentrated in the lenses to a sufficient degree that when the lens is placed in the eye, the concentrated preservatives from the cleaning or disinfecting solution are released and often cause eye irritation. This problem is particularly severe with quaternary ammonium compounds which are concentrated more than four hundred times by hydrophilic lenses.

Contact lenses may be disinfected by using heat disinfection. This method of disinfecting soft contact lenses in conjunction with a preserved saline kills pathogens, but does not kill spores. Further, heat disinfection is not convenient. Subjecting lenses to repeated heat cycles also may reinforce deposited proteins and other materials deposited on the lenses while wearing them. Once allowed to accumulate, substantial effort is required to remove them.

Hydrogen peroxide has been used to clean soft contact lenses and has good germicidal activity. Hydrogen peroxide has a pH of about 3. It is necessary, therefore, to neutralize the lenses with sodium bicarbonate or other means before the lenses can be worn. This is an inconvenient and potentially dangerous procedure.

isotonic sterilizing solutions containing chlorhexidine have been used to preserve contact lens solutions. Chlorhexidine is inactivated by many peptides, proteins and fatty substances of natural origin and forms insoluble precipitates with the latter. The latter phenomenon is adverse to obtaining a sterile and comfortable contact lens. Chlorhexidine is also toxic at high concentrations. Chlorhexidine is concentrated as much as 100 fold by hydrophilic contact lenses which results in the potential for injury to the eye.

The desirability for a composition that can be used as a disinfectant or preservative for contact lenses without causing toxic side effects is readily apparent. All presently known preservatives and disinfectants for ocular use show some degree of ocular irritation. Although heretofore known soft contact lenses exhibit binding or absorption of preservatives and disinfectants, the preservatives and disinfecting system of the present invention has essentially no potential for ocular irritation or binding to soft contact lenses. The invention can be used interchangeably in both thermal disinfection systems and chemical disinfection systems for all types of contact lenses. The invention has significant advantages in terms of toxicity over all kinds of preservatives and disinfectants presently used for disinfection of contact lenses and preserving contact lens solutions. While not intending to be bound by any theory, it is believed that the described preservative and disinfectant has a large polymeric structure which prevents absorption, adsorption or physical binding to contact lens materials. With essentially no potential for ocular irritation, the invention is particularly useful with silicone, hard gas permeable contact lenses, and gel hydrophilic soft contact lenses.

It has now been found that an aqueous solution of a particular polymeric quaternary ammonium compound provides an improved disinfecting solution for contact lenses as well as a preservative for aqueous ocular solutions, suspensions and ointments including contact lens treating solutions, comfort drop solutions and preserved saline solutions. Specifically, the polymeric pharmaceutically acceptable quaternary ammonium compound is 1-tris(2-hydroxyethyl)ammonium-2-butenyl-4-poly[1-dimethyl ammonium-2-butenyl]-w-tris(2-hydroxyethyl)ammonium the salt of which has a pharmaceutically acceptable anion. The salt of the compound has a number average molecular weight generally in the range of from about 2,000 to about 30,000 and preferably in the range of about 3000 to about 14,000. The compound has the general formula:

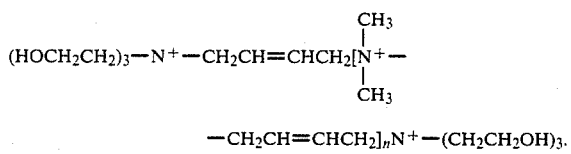

$$-CH_2CH=CHCH_2]_nN^+-(CH_2CH_2OH)_3.$$

The latter compound is a cation which is derived from the disassociation of a salt that has a pharmaceutically acceptable anion such as halogen, such anion preferably being chloride or bromide. The compound provides a disinfectant and preservative yielding unique ophthalmic compositions.

The chloride salt of the disclosed compound is also known as Onamer M which is a registered trademark of Onyx Chemical Company, Jersey City, N.J. As can be seen by the above formula, the quaternary ammonium salt is polymeric. Depending upon the method of measurement, Onamer M in the ophthalmic compositions of the invention preferably has a number average molecular weight between about 3000 to about 14,000, however, as long as the molecular weight of the polymeric quaternary ammonium salt of the invention is sufficiently large so that absorption, adsorption, or physical binding onto soft contact lenses is substantially precluded, aqueous solutions of Onamer M or the quaternary ammonium salt of the invention provide an improved disinfecting solution as well as a preservative for aqueous ocular solutions for such lenses. Hence, the invention not only provides novel disinfecting solutions, but also provides novel preserved aqueous ocular solutions such as cleaning solutions, comfort drop solutions, and preserved saline solutions. Moreover, the quaternary salt of the invention may be used to preserve solutions, suspensions and ointments of ophthalmic medicaments. Heretofore, those who wore contact lenses and who used an ophthalmic medicament faced the problem of having the preservative of the composition containing the medicament concentrate in the contact lens. The quaternary salt of the invention serves as an ideal preservative for ophthalmic compositions wherein the quaternary salt will not concentrate in contact lenses of the patient using the medicament.

Three methods may be used to determine the number average weight of the polymeric ammonium salt used in the invention. These methods include (I) gel permeation chromatography using a polypropylene glycol standard, (II) gel permeation chromatography using a polyvinyl pyridine standard, and (III) nuclear magnetic resonance spectroscopy. In method I the number average molecular weight is determined by comparing the retention time of Onamer M or polymeric salt with a polypropylene glycol standard. With this method the quaternary ammonium salt used in the invention has a molecular weight in the range of about 8000 to 12,000. In method II the number average molecular weight is determined by comparing the retention time of Onamer M or quaternary ammonium salt with a polyvinyl pyridine standard. With this method, the quaternary ammonium salt used in the invention has a molecular weight in the range of about 4100 to about 6000. In method III, using carbon 13 and nuclear magnetic resonance spectroscopy, Onamer M or quaternary ammonium salt used in the invention has a molecular weight in the range of about 3400 to 5000.

It has been found that contact lens solutions containing the quaternary ammonium salt of the invention including Onamer M can be used at ambient temperatures for effective disinfection of contact lenses. Solutions of the quaternary ammonium salt including Onamer M can be used for all types of lens material including PMMA, HEMA polymers and copolymers, silicone-MMA copolymers, silicone, cellulose acetate butyrate, and copolymers with glycerol methylmethacrylate or N-vinyl pyrrolidone with very low risk of ocular irritation or damage to the lens. The subject quaternary ammonium salt is compatible with nonionic surfactants, cationic surfactants, salts of ethylenediamine tetraacetic acid, polyvinyl alcohols, polyvinylpyrrolidone, hydroxypropylmethyl cellulose, sodium chloride and other compounds commonly used in contact lens cleaning, rinsing, wetting, soaking and disinfecting solutions. The subject quaternary ammonium salt is compatible with other antimicrobial agents including thimerosal, benzalkonium chloride, and chlorhexidine. Further, the subject quaternary ammonium salt is compatible with phosphate, borate, carbonate, and citric buffer systems at pH values of 3 to 11. In order to have the desired antimicrobial effectiveness for contact lens solutions, the quaternary ammonium salt of the invention can be used at concentrations in the range of 0.00001% to 3% with the preferred concentration range for a disinfecting solution being from 0.001% to about 0.01%, and the preferred concentration range for the quaternary salt as a preservative being from about 0.0001% to about 005% with all percentages herein being weight/volume or grams per 100 ml of solution. The concentrations relating to the quaternary salt as a disinfectant or preservative are not critical and are merely expressions of preferred ranges. For example, the concentration of the quaternary salt may be in the range of 0.01% by weight/volume and may still act as a preservative.

Contact lens solutions containing the quaternary ammonium salt are compatible with all types of lenses during thermal disinfection at temperatures of 60° C. to 100° C., and during chemical disinfection at ambient temperatures. The contact lens wearer can change from thermal disinfection to chemical disinfection without damaging the lens or concern for potential ocular irritation with contact lens solutions containing the quaternary ammonium salt. The low potential for ocular irritation of a formulation using the quaternary ammonium salt, permits the salt to provide a safe and effective disinfection system for both soft and hard lens contact lenses.

The following illustrate an evaluation with respect to ocular irritation of four aqueous formulations of chemical disinfection systems for contact lenses.

EXAMPLE I

| | |
|---|---|
| Benzalkonium chloride | 0.01% |
| EDTA, disodium salt | 0.1% |
| Sodium chloride | 0.75% |
| Sodium borate | q.s. pH 7.5 |
| Boric acid | 0.35% |

EXAMPLE II

| | |
|---|---|
| Onamer M | 0.01% |
| EDTA, disodium salt | 0.1% |
| Sodium chloride | 0.75% |
| Sodium borate | q.s. pH 7.5 |
| Boric acid | 0.35% |

EXAMPLE III

| | |
|---|---|
| Chlorhexidine digluconate | 0.005% |
| Thimerosal | 0.001% |
| EDTA, disodium salt | 0.1% |
| Sodium chloride | 0.75% |
| Boric acid | 0.35% |
| Sodium borate | q.s. pH 7.0 |

EXAMPLE IV

Normol, a commercial solution sold by Burton, Parsons & Company, Inc. which contains 0.005% chlorhexidine digluconate, 0.001% thimerosal, and 0.1% EDTA.

In the exploratory study of Examples I to IV, the four formulations of the systems were evaluated for ocular irritation potential. The experimental design was (1) ten immersion cycles (8-12 hours per cycle) of polymacon contact lenses in one of four formulations with the lenses being transferred to fresh formulation between each cycle; and (2) placement of the lenses onto eyes of six rabbits for each formulation, right eye only, for an approximate 10 hour wear period for two consecutive days. Following the first day of lens wear, the lenses were reimmersed in fresh formulation overnight. Biomicroscopic examination of the rabbit eyes was performed after each lens wear period (days 1 and 2) as well as at approximately 16 hours (day 3) and 40 hours (day 4) following the second lens wear period.

The result was that the irritative ocular changes in the rabbits which wore polymacon contact lenses exposed to the subject polymeric quaternary ammonium salt formulation, under a regimen more severe than that anticipated clinically, were less in number, severity and incidence than those in rabbits which wore polymacon contact lenses exposed to the other formulations in the examples.

In a further study with respect to ocular irritation and evaluation thereof in rabbits' eyes, the following two formulations of the quaternary ammonium salt were studied.

EXAMPLE V

| | |
|---|---|
| Onamer M | 3.0% |
| Disodium EDTA | 0.1% |
| NaCl | 0.75% |
| Boric Acid | 0.35% |
| Sodium Borate | 0.1% |
| Purified Water | q.s |
| pH | 7.5 |

EXAMPLE VI

| | |
|---|---|
| Onamer M | 0.3% |
| Disodium EDTA | 0.1% |
| NaCl | 0.75% |
| Boric Acid | 0.35% |
| Sodium Borate | 0.1% |
| Purified Water | q.s |
| pH | 7.5 |

The two formulations in Examples V and VI which contained the quaternary ammonium salt were evaluated for ocular irritation. The experimental procedure was (1) immersion of polymacon contact lenses in one of the two formulations for approximately 90 hours; (2) placement of the lenses onto eyes of six rabbits, right eye only, for an approximate 10 hour lens wear period for two consecutive days. Following the first day of lens wear, the lenses were reimmersed in fresh formulation overnight. Biomicroscopic examination of the rabbit eyes were performed following each lens wear period (days 1 and 2) as well as at approximately 16 hours (3 days) following the second lens wear period.

Biomicroscopic examinations of the rabbit eyes in which the soft contact lenses were worn and treated with the 3.0% Onamer M formulation revealed minimal-moderate conjunctival congestion, minimal conjunctival swelling, minimal corneal cloudiness and a single incidence of flare. Minimal-moderate congestion, minimal swelling, minimal conjunctional discharge, and minimal corneal cloudiness were observed on the rabbits which wore the lenses treated with the 0.3% Onamer M formulation.

Further in vitro and in vivo toxicology studies were conducted as to Onamer M. The effect of Onamer M on the corneal epithelium of rabbits was tested by the "Conjunctive Cup" exposure model. Comparative data was obtained as to benzalkonium chloride, thimerosal, chlorhexidine and Onamer M. The following solutions were made in GBR (physiological saline solutions):
(1) 0.01% weight/volume benzalkonium chloride;
(2) 0.005% weight/volume themerosal;
(3) 0.005% weight/volume chlorhexidine;
(4) 0.01% weight/volume Onamer M; and
(5) 0.001% weight/volume Onamer M.

Rabbits were anesthesized, one eye was used as a control and one eye was exposed to the solution by bathing it with the use of a cup with the test solution for 15, 30 and 60 minutes. The corneal epithelium then was analyzed by a scanning electron microscope (SEM) which renders a three dimensional view of the corneal epithalium. The results of the study were as follows:

A. Benzalkonium chloride caused severe damage to primary and secondary layers of the corneal epithalium in 15 minutes.

B. Thimerosal caused loss of the primary cell layer at 30 minutes; there was minimal damage (junction loss) to the secondary cell layer at 60 minutes.

C. Chlorhexidine caused loss of the primary cell layer at 30 minutes; there was minimal damage to secondary cell layer at 60 minutes.

D. Onamer M at the 0.01% concentration caused loss of the primary cell layer at 15 minutes; there was secondary cell loss at 60 minutes.

E. With Onamer M at the 0.001% concentration the primary cell layer was intact with very slight membrane damage at 60 minutes.

In an in vitro test the effect of Onamer M and other solutions on rabbit corneal endothelium were studied by a SEM and a transmission election microscope (TEM), the latter reducing a two-dimension view of the sample. In this study the rabbit corneal endothelium were removed from the rabbit, mounted and perfused with the test solution for two hours. The following test solutions were prepared in GBR (physiological saline solutions):
(1) 0.01% weight/volume benzalkonium chloride;
(2) 0.005% weight/volume thimerosal;
(3) 0.005% weight/volume chlorhexidine;
(4) 0.01% weight/volume Onamer M; and
(5) 0.001% weight/volume Onamer M.

SEM and TEM specular microscopic studies yielded the following results:

A. Benzalkonium chloride caused severe corneal endothelial damage; there was immediate marked corneal swelling.

B. Thimerosal caused moderate-severe corneal endothelial damage (loss of junctions and cell vacularization); there was delayed onset of moderate-severe swelling (1 hour).

C. With chlorhexidine there was time dependent loss of cells (total cell loss) moderate damage after 2 hours; there was a delayed onset of moderate swelling (1 hour).

D. The 0.01% Onamer M solution caused severe corneal endothelial damage at 1 hour; there was moderate swelling at 1 hour.

E. The 0.001% Onamer M solution caused minimal corneal endothelial damage (mild vacularization); there was delayed onset of moderate swelling at approximately 1 hour.

The ability of the quaternary amnonium salt to resist neutralization by organic soil (a mixture of serum and killed yeast cells) was determined by testing 0.01%, 0.001% and 0.0001% formulations of the salt against *Staphylococcus aureus* and *Pseudomonas aeruginosa* in the presence of serum and killed yeast cells. Similar concentrations of benzalkonium chloride were tested as controls. The antimicrobial activity of a 0.001% formulation of the quaternary ammonium salt solution was neutralized by organic soil against both *Staphylococcus aureus* and *Pseudomonas aeruginosa*. The antimicrobial activity of a 0.01% formulation of the quaternary ammonium salt was not neutralized against either test organism. Similar results were obtained with the 0.0001% and 0.01% concentrations of benzalkonium chloride. Test results as to the ability of Onamer M to resist neutralization by organic soil are illustrated in Table I.

TABLE I

ABILITY OF ONAMER M
TO RESIST NEUTRALIZATION BY ORGANIC SOIL
Time (minutes) to Kill 4 $\text{Log}_{10}$

| | No Organic Soil | | Organic Soil* | |
|---|---|---|---|---|
| Concetration | S. Aureus | P. Aeruginosa | S. Aureus | P. Aeruginosa |
| 0.01% Onamer M | <10 | <10 | <10 | <10 |
| 0.001% Onamer M | 30 | <10 | 60 | >240 |
| 0.0001% Onamer M | >240 | >240 | >240 | >240 |
| 0.01% benzalkonium chloride | <10 | <10 | <10 | <10 |
| 0.001% benzalkonium chloride | <10 | <10 | <10 | >240 |
| 0.0001% benzalkonium chloride | >240 | >240 | >240 | >240 |

*Organic Soil = Serum and killed yeast cells.

The preservative protectiveness of the quaternary ammonium salt was determined with solutions of 0.001%, 0.01% and 0.1% of Onamer M. A solution of 0.01% benzalkonium chloride was used as a control. All solutions contained 0.05% disodium edetate, 0.75% sodium chloride and borate buffer at pH 7.5. All solutions were tested by both the USP XIX, and FDA Preservative Effectiveness tests. A significant organic load was included in the challenge with FDA Preservative Test.

All three concentrations of the Onamer M solution met the criteria of both the USP XIX, and FDA Preservative Effectiveness Tests against all of the test organisms. The 0.01% benzalkonium chloride control solution also met the criteria of both tests. The Onamer M formulations were effective in reducing concentrations of *Staphylococcus aureus, C. albicans, Pseudomonas aeruginosa*, and *E. coli* to less than 0.1% of the initial concentrations of each organism after 14 days.

The Onamer M formulations were also effective in reducing the initial concentration of *A. niger* by 2 $\log_{10}$ after 14 days in both tests.

Table II illustrates comparative antimicrobial activity of Onamer M formulations and benzalkonium chloride. In the test the results of which are shown in Table II, approximately 10,000 or 1,000,000 organisms were exposed to 1 ml of the different formulations shown. Each type of organisms had the same organism population for the various formulations tested on the organism. The numbers in the table are the times required by each formulation to kill all organisms present. As shown Onamer M was effective in 30 minutes against *Staphylococcus epidermidis, Serratia marcescens, Pseudomonous aeruginosa*, and *Candida albicans*.

TABLE II

COMPARATIVE ANTIMICROBIAL ACTIVITY OF
ONAMER M AND BENZALKONIUM CHLORIDE
Time to Kill $10^4$–$10^6$ $\log_{10}$ (minutes)

| SOLUTION | S. Epidermidis | S. Marcscens | P. Aeruginosa | C. Albicans | A. Fumigatus |
|---|---|---|---|---|---|
| 0.001% Onamer M | <10 | 30 | <10 | <10 | >240 |
| 0.0001% Onamer M | 30 | 30 | 30 | <10 | >240 |
| 0.00001% Onamer M | 120 | >240 | >240 | >240 | >240 |
| 0.0001% BAC | <10 | 30 | <10 | <10 | 240 |
| 0.00001% BAC | <10 | 240 | 30 | 240 | >72 hrs |

Additional tests indicate that Onamer M has activity against bacteria and yeast, but only static activity against some fungi and fungicidal against *Fusavium Solani*. However, the fungicidal activity of Onamer M formulation can be enhanced with the addition of mixtures of thimerosal, polyvinyl alcohol (PVA), as well as the addition of polyvinyl pyrrolidone (PVP). More particularly, tests indicate that such fungicidal activity was increased two-fold against *A. niger* and *A. fumigatus* with the addition of 0.01% of 0.2% PVP to a 0.2% solution of Onamer M. The addition of 0.01% to 0.2% PVA to a 0.2% solution of Onamer M and 0.001% to 0.005% solution of thimerosal enhanced the fungicidal activity of the solution against *A. niger* by two-fold and slightly against *A. fumigatus*. However, the addition of 0.001% to 0.002% by weight of thimerosal to solutions of Onamer M failed to significantly enhance the activity of the solution against *A. fumigatus*. Solutions of Onamer M did not show a kill of *A. fumigatus* at concentrations of 30% in four hours.

To determine if quaternary ammonium salt of the invention is bound and released by soft contact lenses zone of growth inhibition tests were conducted with Onamer M. Comparative tests were conducted by placing approximately 10,000 organisms/ml in agar gelatin. Individual polymacon soft contact lenses were soaked in Onamer M, benzalkonium chloride and commercial Flexsol (which is sold by Burton, Parsons & Company, Inc.) solutions for 24 hours prior to determining zone of growth inhibition. After soaking, the lenses were rinsed of residual solution with distilled water and placed onto the agar gelatin with the microorganisms. The comparative results for zone of growth inhibition against *S. aureus* using the Onamer M, benzalkonium chloride, and the commercial Flexsol solution are shown in Table III. The tests indicate little if any Onamer M is bound and/or released by the contact lens. The results also show significant zones of growth inhibition by the lenses soaked in Flexsol (chlorhexidine) solution and benzalkonium chloride solution, indicating that these two antimicrobials are bound and released by contact lenses.

TABLE III

ZONE OF INHIBITION RESULTS WITH LENSES
SOAKED IN ONAMER M SOLUTIONS AGAINST *S. aureus*

| Solution | Zone of Growth Inhibition (mm) Against *S. aureus* |
|---|---|
| 0.01% Onamer M | 0 |
| 0.001% Onamer M | 0 |
| 0.001% BAC | 22 |

TABLE III-continued
ZONE OF INHIBITION RESULTS WITH LENSES
SOAKED IN ONAMER M SOLUTIONS AGAINST *S. aureus*

| Solution | Zone of Growth Inhibition (mm) Against *S. aureus* |
|---|---|
| Flexsol | 24 |

The comparative cellular toxicity of soft contact lenses soaked in Onamer M at various concentrations and other solutions was determined by in vitro testing. Mouse cells were grown on a basal salts media using standard tissue culture techniques. Mouse cells were obtained from Microbiological Associates, 4733 Bethesda Avenue, Bethesda, Md. The cells were identified as Mouse L929 cells. The cells were grown until confluent growth was obtained. HEMA soft contact lenses were cycled through seven 8 hour cycles of fresh solution prior to exposure to the mouse cells. After soaking, the lenses were rinsed in water. The mouse cells were then exposed to each respective lens for 24 hours, whereupon the cell growth was examined microscopically and with staining procedures. The effect of aqueous Onamer M at various concentrations and other solutions are shown in Table IV.

TABLE IV
COMPARATIVE CYTOTOXICITY OF
SOFT CONTACT LENSES SOAKED
IN PRESERVED SOLUTIONS
ON MOUSE L929 CELLS

| | Cytotoxic Response | | |
|---|---|---|---|
| Lens Soaked | Cell Lysis | Zone of Cell Death (mm) | Cytotoxicity Conclusion[b] |
| Saline | − | 0 | None |
| 0.001% Onamer M | − | 0 | None |
| 0.01% Onamer M | − | 0 | None |
| 0.01% Onamer M | − | 0 | None |
| 0.01% Onamer M | − | 0 | None |
| 0.1% Onamer M | − | 0 | None |
| 0.3% Onamer M | − | 0 | None |
| 1.0% Onamer M | + | 31 | Moderate |
| Alkyltriethanol Ammonium[a] Chloride (0.03%) + Thimerosal (0.002%) | + | 16 | Minimal |
| Chlorhexidine (0.005%)[a] + Thimerosal (0.001%) | + | 25 | Moderate |
| Thimerosal (0.001%)[a] | + | 10 | Minimal |
| Sorbic Acid (0.1%)[a] | + | 16 | Minimal |
| 0.01% Benzalkonium Chloride | + | 48 | Severe |
| 0.01% Benzalkonium Chloride | + | 64 | Severe |

[a]Commercially available marketed solutions.
[b]Cytotoxicity was rated as follows:
Minimal: when the zone of decolorization was 20 mm
Moderate: when the zone of decolorization was 20-40 mm
Severe: when the zone of decolorization was 40 mm The quaternary ammonium salt of the invention including Onamer M provides an excellent material to preserve and provide novel ophthalmic solutions including but not limited to comfort drop solutions and contact lens treating solutions, such as cleaning solutions and preserved saline solutions. Cleaning solutions of the invention include Onamer M, anionic or cationic surfactants, NaCl, chelating agents such as EDTA or salts thereof for chelating metals and enhancing antimicrobial activity, buffers such as borates or phosphates and optionally wetting agents such as polyvinyl alcohol (PVA), polyvinyl pyrrolidone (PVP), hydroxypropyl methyl cellulose, hydroxyethyl cellulose and polyvidone. The preserved comfort drop solutions of the invention include NaCl, buffers as previously described, wetting agents as previously described and Onamer M. The preserved disinfecting saline solutions of the invention include Onamer M, NaCl, buffers as previously described and EDTA or salts thereof.

Examples VII to XII are examples of ophthalmic solutions which may be preserved with Onamer M, such solutions including preserved saline solutions, cleaning solutions, and comfort drop solutions.

EXAMPLE VII

| Preserved Saline Solution | |
|---|---|
| Onamer M | 0.001% |
| NaCl | 0.75% |
| Disodium edetate | 0.05% |
| Boric acid | 0.35% |
| Sodium borate | 0.1% |
| Water | q.s. |
| pH | 7.0-7.5 |

EXAMPLE VIII

| Cleaning Solution | |
|---|---|
| Onamer M | 0.001% |
| Disodium edetate | 0.05% |
| Pluronic F68 | 5.0% |
| Pluronic L64 | 1.0% |
| Boric acid | 0.35% |
| Sodium borate | 0.5% (pH 8.0) |
| Water | q.s. |

EXAMPLE IX

| Comfort Drop Solution* | |
|---|---|
| Onamer M | 0.001% |
| Disodium edetate | 0.1% |
| Hydroxypropyl methylcellulose | 0.4% |
| NaCl | 0.75% |
| Potassium Chloride | 0.12% |
| Water | q.s. |
| Sodium hydroxide | pH 7.5 |

*A solution used during contact lens wear which provides lubrication and wetting of the contact lens in the eye.

EXAMPLE X

| Comfort Drop Solution | |
|---|---|
| | % W, V |
| Onamer M | 0.01% |
| Dextran 70, 75* | 0.01% |
| Edetate Disodium | 0.01% |
| Sodium Chloride | 0.77% |
| Potassium Chloride | 0.12% |
| Hydroxy Methyl Cellulose 2910 | 0.30% |
| Purified Water q.s. | |

*A polysaccharide filler to add viscosity and lubricity, the filler constituting αD-gluco pyanosyl units.

EXAMPLE XI

| Artifical Tear Solution* | |
|---|---|
| | % W,V |
| Onamer M | 0.01% |
| Dextran T 70,75** | 0.10%. |
| Edetate Disodium | 0.10% |

-continued

| Artifical Tear Solution* | |
|---|---|
| | % W,V |
| Hydroxy Methyl Cellulose 2910 | 0.30% |
| Potassium Chloride | 0.12% |
| Sodium Chloride | 0.77% |
| Purified Water | q.s. |

*A solution used to obviate dry eye symptoms by increasing or producing extended tear break up time.
**A polysaccharide filler to add viscosity and lubricity, the filler constituting αD-Gluco pyanosyl units.

EXAMPLE XII

| Wetting and Soaking Solution for Contact Lenses* | |
|---|---|
| | % W,V |
| Onamer M | 0.001% |
| Edetate Disodium | 0.1% |
| Hydroxyethyl Cellulose 15,000 | 0.75% |
| Polyvinyl Alcohol | 0.75% |
| Sodium Biphosphated | 0.017% |
| Sodium Chloride | 0.46% |
| Sodium Phosphate | 0.67% |
| Tween 80 | 0.05% |
| Purified Water | q.s. |

*A solution which is used with hydrophobic rigid or semi-rigid contact lenses such as PMMS, Silicone and PMMA, Acrylate lenses to enhance the wetability of the lenses.

EXAMPLE XIII

| Comfort Drop Solution | |
|---|---|
| | % W,V |
| Onamer M | 0.01% |
| Edetate Disodium | 0.10% |
| Adsorbobase | 0.20% |
| Providone | 1.67% |
| Sodium Biphosphate | 0.10% |
| Sodium Chloride | 0.30% |
| Sodium Phosphate | 0.88% |
| Purified Water | q.s. |

The formulations of Examples VII to XIII are only illustrative of solutions which can be preserved with Onamer M. These solutions may also contain and are not limited to the following components to obtain desired solution characteristics: Sodium phosphate, propylene glycol 4000, PVP, PVA, triethanolamine, and non-ionic surfactants including Pluronic (which is a registered trademark of Wyandotte Chemicals Corp) P65, F65, P123, L63, and Tween 80 (which is a registered trademark of Atlas Powder Company).

Moreover, the quaternary ammonium salt of the invention may be used as a preservative with solutions, suspensions and ointments of ophthalmic medicaments. Examples of these compositions include:

EXAMPLE XIV

The following constituents are combined to formulate an ophthalmic topical anesthetic solution.

| | W,V |
|---|---|
| Proparacaine Hydrochloride | 8.0% |
| Glycerin | 2.5% |
| Onamer M | 0.01% |
| Purified Water | q.s. |

EXAMPLE XV

The following constituents are combined to formulate an ocular lubricant ointment.*

| | W,V |
|---|---|
| Mineral Oil | 3.0% |
| Anhydrous Liquid Lanolin | 3.0% |
| Onamer M | 0.01% |
| White Petrolatum | q.s. |

*An ointment being a semi-solid composition for topical application to the eye.

EXAMPLE XVI

The following constituents are combined to formulate an ophthalimic irrigating solution.

| | W,V |
|---|---|
| Sodium Chloride | 0.49% |
| Potassium Chloride | 0.075% |
| Calcium Chloride | 0.048% |
| Magnesium Chloride | 0.03% |
| Sodium Acetate | 0.39% |
| Sodium Citrate | 0.17% |
| Onamer M | 0.001% |
| Purified Water | q.s. |

EXAMPLE XVII

The following constituents are combined to formulate an ophthalimic solution for control of intraocular pressure.

| | W,V |
|---|---|
| Pilocarpine Hydrochloride | 3.0% |
| Boric Acid | 1.5% |
| Sodium Citrate | 0.1% |
| Onamer M | 0.001% |
| Purified Water | q.s. |

EXAMPLE XVIII

The following constituents are combined to formulate an ophthalimic carticosteriod suspension*.

| | W/V |
|---|---|
| Dexamethasone | 0.1% |
| Sodium Phosphate | 0.2% |
| Polysorbate 80 | 0.05% |
| Edetate Disodium | 0.01% |
| Sodium Chloride | 0.7% |
| Hydroxy Propyl Methylcellulose | 0.17% |
| Onamer M | 0.001% |
| Purified Water | q.s. |

*A suspension being defined as a composition which includes finely divided, undissolved agents dispersed in a liquid vehicle.

EXAMPLE XIX

The following constituents are combined to formulate an anti-infective steriod combination in suspension.

| | W/V |
|---|---|
| Polymyxin B Sulfate | 6000 units/ml |
| Neomycin Sulfate | 3.5 mg base/ml |
| Dexamethasone | 0.1% |
| Sodium Chloride | 0.85% |
| Polysorbate 20 | 0.05% |
| Hydroxy Propyl Methylcellulose | 0.5% |
| Onamer M | 0.001% |
| Purified Water | q.s. |

EXAMPLE XX

The following constituents are combined to formulate an antichalinergic agent.

| | W/V |
|---|---|
| Tropicamide | 0.5% |
| Sodium Chloride | 0.8% |
| Edetate Sodium | 0.01% |
| Onamer M | 0.001% |
| Purified Water | q.s. |

EXAMPLE XXI

The following constituents are combined to formulate an ophthalmic decongestant solution.

| | W/V |
|---|---|
| Naphazoline hydrochloride | 0.012% |
| Boric Acid | 1.0% |
| Sodium Chloride | 0.35% |
| Potassium Chloride | 0.042% |
| Edetate Disodium | 0.05% |
| Onamer M | 0.001% |
| Purified Water | q.s. |

EXAMPLE XXII

The following constituents are combined to formulate an ophthalmic solution containing an antihistamine.

| | W/V |
|---|---|
| Pheniramine Maleate | 0.3% |
| Naphazoline Hydrochloride | 0.025% |
| Boric Acid | 1.0% |
| Sodium Borate | 0.15% |
| Edetate Disodium | 0.01% |
| Sodium Chloride | 0.2% |
| Onamer M | 0.001% |

EXAMPLE XXIII

The following constituents are combined to formulate an antiinfective ophthalmic solution.

| | W/V |
|---|---|
| Tobramycin | 0.3% |
| Tyloxapol | 0.1% |
| Boric Acid | 1.24% |
| Sodium Sulfate | 0.152% |
| Sodium Chloride | 0.278% |
| Onamer M | 0.001% |
| Purified Water | q.s. |

Examples XIV and XXV are examples of contact lens disinfecting solutions which contain Onamer M alone or in combination with other antimicrobial agents.

EXAMPLE XXIV

| | |
|---|---|
| Onamer M | 0.01% |
| Sodium chloride | 0.2% |
| Propylene glycol | 1.2% |
| Disodium edetate | 0.05% |
| Boric acid | 0.35% |
| Sodium borate | 0.3% |
| Water | q.s. |
| pH | 7.0-7.5 |

EXAMPLE XXV

| | |
|---|---|
| Onamer M | 0.01% |
| Thimerosal | 0.001% |
| Disodium EDTA | 0.05% |
| PVP | 0.2% |
| Sodium chloride | 0.85% |
| Boric acid | 0.35% |
| Sodium borate | 0.4% |
| Water | q.s. |
| pH | 7.0-7.5 |

The addition of thimerosal in the formulation of Example XXV enhances the fungicidal activity of Onamer M. The formulations of the Examples are only illustrative and also may contain and are not limited to the following components to obtain desired characteristics: Sodium phosphate, propylene glycol, PVP, PVA, non-ionic surfactants including Pluronic P65, F65, P123, L63, and Tween 80, and antimicrobial agents including phenylmercuric nitrate, phenylmercuric acetate, and phenylethyl alcohol.

EXAMPLE XXIV

A particularly unique composition of the invention is a contact lens cleaner which includes polymeric particles and wherein the polymeric quatenary salt of the invention is used as a disinfectant and/or preservative for the cleaner. The use of polymeric beads or particles as a contact lens cleaner is described in United States application Ser. No. 470,181 filed Feb. 28, 1983 which is fully incorporated herein. An example of such composition is as follows:

| | % W,V |
|---|---|
| Polymer Beads | 10.0% |
| Sodium Chloride | 0.6% |
| Boric Acid | 0.2% |
| Edetate Disodium | 0.1% |
| Onamer M | 0.01% |
| Sodium Borate | 0.25% |
| Tween 21 | 0.5% |
| Hydroxy Ethyl Cellulose 15,000 | 0.8% |
| Purified Water | q.s. |

It will be seen that the invention provides new, useful and novel disinfecting and preserved ocular compositions including contact lens disinfecting, soaking and storage compositions for decontamination for both hard and soft contact lenses. The invention also may be used as a disinfectant and preservative in contact lens cleaning, wetting and lubricating solutions. Additionally, quaternary ammonium salt including Onamer M may be used as a preservative for ophthalmic compositions used for dilation, treatment of glaucoma, antimicrobial therapy, ocular anti-inflammatory therapy, anesthetic, treatment of dry eye, diagnostic evaluation, adjuncts to surgery, chelating agents, and immunosuppressive agents.

The invention in its broader aspects is not limited to the specific details shown and described, but departures may be made from such details within the scope of the accompanying claims without departing from the principles of the invention and without sacrificing its advantages.

What is claimed is:

1. An aqueous ophthalmic contact lens solution comprising:
   from about 0.00001 to about 3.0 percent by weight/volume of a quaternary ammonium compound having a number average molecular weight in the range of about 2,000 to about 30,000, said compound having the formula

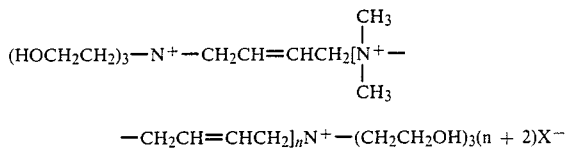

wherein X = a pharmaceutically acceptable anion;
   an effective amount of NaCl to provide isotonicity to said solution; and
   an effective amount of buffer to provide said solution with an ophthalmically acceptable pH.

2. An aqueous ophthalmic solution as recited in claim 1 wherein said solution further comprises a wetting agent.

3. An aqueous ophthalmic solution as recited in claim 2 wherein said solution further comprises a chelating agent and a surfactant.

4. The ophthalmic solution as recited in claims 1, 2 or 3 wherein the quaternary ammonium compound has a molecular weight in the range of from about 3,000 to about 14,000.

5. An ophthalmic solution as recited in claim 1 wherein said solution is a preserved saline solution.

6. An ophthalmic solution as recited in claim 1 wherein said solution is a preserved disinfecting solution for a soft contact lens.

7. An ophthalmic solution as recited in claim 2 wherein said solution is a preserved comfort drop solution.

8. An ophthalmic solution as recited in claim 3 wherein said solution is a cleaning solution.

9. An aqueous ophthalmic solution as recited in claim 1 wherein X = Cl$^-$.

10. An aqueous ophthalmic soft contact lens solution as recited in claim 1 wherein said contact lens is a soft contact lens.

11. An aqueous ophthalmic soft contact lens solution as recited in claim 1 or 10 wherein said anion is Cl$^-$.

12. The aqueous ophthalmic soft contact lens solution as recited in claim 1 wherein said quaternary ammonium compound has a molecular weight sufficiently large to substantially preclude adsorption, absorption or physical binding onto a soft contact lens.

13. An aqueous ophthalmic soft contact lens solution as recited in claim 12 wherein said solution further comprises a wetting agent.

14. An aqueous ophthalmic soft contact lens solution as recited in claim 12 wherein said anion is Cl$^-$.

15. An aqueous ophthalmic soft contact lens solution as recited in claim 13 wherein said solution further comprises a chelating agent and a surfactant.

16. An ophthalmic soft contact lens solution as recited in claims 12, 13, 14 or 15, wherein the quaternary ammonium compound has a molecular weight in the range of from about 3,000 to about 14,000.

17. An isotonic contact lens disinfecting solution comprising from about 0.001 to about 0.01 percent by weight/volume of a quaternary ammonium compound having a number average molecular weight in the range of about 2,000 to about 30,000, said quaternary ammonium compound having the formula

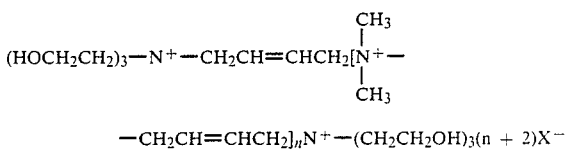

wherein X = a pharmaceutically acceptable anion;
an effective amount of NaCl to provide isotonicity to said solution;
an effective amount of a buffer to provide said solution with an ophthalmically acceptable pH.

18. A contact lens disinfecting solution as recited in claim 17 wherein said quaternary ammonium compound has a molecular weight in the range of from about 3,000 to about 14,000.

19. An isotonic contact lens disinfecting solution as recited in claims 17 or 18 wherein said solution further includes ethylenediaminetetracetic acid or salts thereof and a wetting agent selected from the group consisting of polyvinyl alcohol, polyvinyl pyrrolidone, hydroxypropyl methyl cellulose, hydroxyethyl cellulose, polyvidone and mixtures thereof.

20. An isotonic contact lens disinfecting solution as recited in claim 18 wherein X = Cl$^-$.

21. A method of imparting antimicrobial activity to an aqueous ophthalmic contact lens solution comprising:
   adding to said solution from about 0.00001% to about 3.0% by weight/volume of a quaternary ammonium salt as an antimicrobial agent having a molecular weight in the range of about 3,000 to about 14,000, said quaternary ammonium salt having the formula

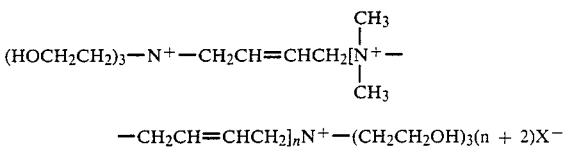

wherein X = a pharmaceutically acceptable anion.

22. A method as recited in claim 21 wherein said antimicrobial agent preserves said solution and wherein said ammonium salt comprises from about 0.0001% to about 0.005% by weight/volume of said solution.

23. A method as recited in claim 21 wherein said antimicrobial agent comprises from about 0.001% to about 0.01% by weight/volume of said solution and wherein said solution disinfects a contact lens.

24. A method as recited in claims 21, 22 or 23 wherein the pharmaceutically acceptable anion is Cl$^-$.

25. A method as recited in claims 21, 22 or 23 wherein the pharmaceutically acceptable anion is Br$^-$.

* * * * *

UNITED STATES PATENT AND TRADEMARK OFFICE
CERTIFICATE OF CORRECTION

PATENT NO. : 4,525,346    Page 1 of 3
DATED : JUNE 25, 1985
INVENTOR(S) : RAYMOND L. STARK It is certified that error appears in the above-identified patent and that said Letters Patent is hereby corrected as shown below:

IN THE ABSTRACT

Change the phrase "as well as a preserved ocular compositions" to --as well as preserved ocular compositions--; and After "treating solutions" insert a --,-- (comma).

IN THE SPECIFICATION

Column 1, line 8, (312 Amendment) after "1981" insert a --,-- (comma);

line 25, change "poly(hydroxyalkyl)" to --poly(hydroxylalkyl)--;

line 30, after "i.e." insert a --,-- (comma); and line 64, change "isotonic" to --Isotonic--.

Column 3, line 25, change "chromotography" to --chromatography--; and line 26, change "chromotography" to --chromatography--.

Column 4, line 6, change "005%" to --0.005%--.

Column 5, line 30, after "q.s" insert a --.-- (period); and line 40, after "q.s" insert a --.-- (period).

Column 6, line 6, change "themerosal" to --thimerosal--;

line 16, change "epithalium" to --epithelium--;

lines 18-19, change "epithalium" to --epithelium--;

line 35, change "election" to --electron--;

UNITED STATES PATENT AND TRADEMARK OFFICE
CERTIFICATE OF CORRECTION

PATENT NO. : 4,525,346

DATED : JUNE 25, 1985

INVENTOR(S) : RAYMOND L. STARK

It is certified that error appears in the above-identified patent and that said Letters Patent is hereby corrected as shown below:

Column 6, line 36, change "reducing" to --rendering--;

line 46, change "microscopic" to --microscope--; and line 66, change "amnonium" to --ammonium--.

Column 7, line 5, change "0.001%" to --0.0001%--;

line 44, change "tests" to --Tests--; and line 64, change "organisms" to --organism--.

Column 8, line 8, change "Marcscens" to --Marcescens; and line 28, in the second instance, change "of" to --to--.

Column 10, line 51, change "% W,V" to --% W/V--;

line 53, change "70,75*" to --70/75*--;

line 58, after "Water" delete "q.s." and insert --q.s.-- under column "% W/V";

line 65, change "% W,V" to --% W/V--; and line 67, change "70,75" to --70/75--.

Column 11, line 3, change "% W,V" to --% W/V--;

line 18, change "% W,V" to --% W/V--;

line 28, change "PMMS, Silicone" to --PMMS/Silicone--;

line 28, change "PMMA, Acrylate" to --PMMA/Acrylate--;

line 35, change "% W,V" to --% W/V--;

UNITED STATES PATENT AND TRADEMARK OFFICE
CERTIFICATE OF CORRECTION

PATENT NO. : 4,525,346

DATED : JUNE 25, 1985

INVENTOR(S) : RAYMOND L. STARK

It is certified that error appears in the above-identified patent and that said Letters Patent is hereby corrected as shown below:

Column 11, line 52, after "Corp" insert a --.-- (period); and
          line 65, change "W,V" to --% W/V--.

Column 12, line 3, change "W,V" to --% W/V--;
          line 12, change "W,V" to --% W/V--;
          line 21, change "ophthalimic" to --ophthalmic--;
          line 24, change "W,V" to --% W/V--;
          line 36, change "ophthalimic" to --ophthalmic--;
          line 40, change "W,V" to --% W/V--;
          line 50, change "ophthalimic" to --ophthalmic--; and
          line 53, change "W,V" to --% W/V--.

Column 14, line 38, change "XXIV" to --XXVI--.

IN THE CLAIMS

Column 16, line 38 change "18" to --17--.

Signed and Sealed this

Twenty-ninth Day of July 1986

[SEAL]

Attest:

DONALD J. QUIGG

Attesting Officer

Commissioner of Patents and Trademarks